(12) United States Patent
Soscia et al.

(10) Patent No.: US 8,349,362 B2
(45) Date of Patent: *Jan. 8, 2013

(54) DOSAGE FORMS FOR TAMPER PRONE THERAPEUTIC AGENTS

(75) Inventors: Anthony Edward Soscia, Atlanta, GA (US); Yingxu Peng, Pennington, NJ (US); Yichun Sun, Germantown, TN (US); James R. Johnson, Germantown, TN (US); Atul J. Shukla, Cordova, TN (US)

(73) Assignee: Atlantic Pharmaceuticals, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/454,235

(22) Filed: Apr. 24, 2012

(65) Prior Publication Data

US 2012/0207797 A1 Aug. 16, 2012

Related U.S. Application Data

(63) Continuation of application No. 11/526,502, filed on Sep. 25, 2006, now Pat. No. 8,187,636.

(51) Int. Cl.
*A61K 9/14* (2006.01)
*A61K 9/20* (2006.01)
(52) U.S. Cl. ........ 424/480; 424/465; 424/472; 424/478; 424/489
(58) Field of Classification Search ................. 424/10.4, 424/400, 451, 464, 465, 471, 472, 476, 478–480, 424/489
See application file for complete search history.

(56) References Cited

U.S. PATENT DOCUMENTS

| | | | |
|---|---|---|---|
| 3,980,766 A | 9/1976 | Shaw | |
| 4,070,494 A | 1/1978 | Hoffmeister | |
| 5,968,542 A | 10/1999 | Tipton | |
| 6,218,440 B1 | 4/2001 | Kitagawa | |
| 6,277,384 B1 | 8/2001 | Kaiko | |
| 6,309,668 B1 | 10/2001 | Bastin | |
| 6,387,404 B2 | 5/2002 | Oshlack | |
| 2002/0032245 A1 | 3/2002 | Hughes | |
| 2002/0146384 A1 | 10/2002 | Hughes | |
| 2002/0176842 A1 | 11/2002 | Hughes | |
| 2003/0068392 A1 | 4/2003 | Sackler | |
| 2003/0124185 A1 | 7/2003 | Oshlack | |
| 2004/0062812 A1 | 4/2004 | Maloney | |
| 2004/0131552 A1 | 7/2004 | Boehm | |
| 2004/0202717 A1 | 10/2004 | Mehta | |
| 2005/0013792 A1 | 1/2005 | Hollenbeck | |
| 2005/0063909 A1 | 3/2005 | Wright | |
| 2005/0236741 A1 | 10/2005 | Arkenau | |
| 2006/0083690 A1 | 4/2006 | Chang | |

*Primary Examiner* — Michael G Hartley
*Assistant Examiner* — Jagadishwar Samala
(74) *Attorney, Agent, or Firm* — Howard Eisenberg, Esq.

(57) ABSTRACT

A dosage form from which a burst release of a drug contained within a tampered dosage form is reduced or retarded by the presence in or on the dosage form of a TPTA (Tamper Prone Therapeutic Agent) trap. If the dosage form has not been tampered with, the TPTA trap does not significantly interfere with the rate of release of the drug from the dosage form. However, if the dosage form has been physically tampered with, the TPTA trap reduces or retards burst release of the drug from the dosage form.

7 Claims, 12 Drawing Sheets

DOSAGE FORMS FOR TAMPER PRONE THERAPEUTIC AGENTS

This application is a continuation application of pending U.S. patent application Ser. No. 11/526,502, filed Sep. 25, 2006.

FIELD OF THE INVENTION

The invention pertains to the field of pharmaceutical compositions that contain systems to deter tampering and abuse of therapeutic agents.

BACKGROUND OF THE INVENTION

Therapeutic pharmaceuticals are often the subject of tampering. Tampering of pharmaceutical products exists in two primary forms: unintended and illicit. In the case of unintended tampering, a therapeutic dosage form is innocently manipulated in a fashion that is not indicated with its dosing instructions. Unintended tampering can exist in many forms. Examples of unintended mechanical tampering include the elderly patient who cannot swallow a large sustained release tablet and, as a result, may crush or dissolve the tablet to make it easier to swallow. Alternatively, a health care worker may take a sustained release tablet and break it to allow for a reduced therapeutic dose. As shown in these examples, the mechanism by which a sustained release dosage form controls the release rate of the drug in vivo may be inadvertently destroyed by physically modifying the dosage form.

Illicit use of pharmaceutical products occurs when an individual knowingly tampers with a dosage form and administers it for a use that is not indicated with its dosing instructions. The purpose for the illicit tampering of a sustained release dosage form is to obtain a burst release of the active ingredient contained in the dosage form. Common physical methods for both illicit and unintentional tampering include chewing, crushing, and grinding with or without the aid of a mechanical device such as a coffee grinder, hammer, household blender or similar devices.

The illicit use of controlled prescription pharmaceuticals is currently an area of increasing concern. Many classes of therapeutic drugs are considered to be Tamper Prone Therapeutic Agents (TPTA). For example, opioid therapeutic agents are often the source of TPTA. Opioids include a diverse group of drugs, natural and synthetic, that have opium- or morphine-like properties and that bind to one of several subspecies of opioid receptors in the body. These drugs produce their major effects on the central nervous system and bowel. The effects of opioids or pseudo-opioids are remarkably diverse and include analgesia, drowsiness, changes in mood, and alterations of the endocrine and autonomic nervous systems. Opioid analgesics comprise the major class of therapeutic agents utilized in the management of moderate to severe pain.

In some individuals, opioids alter mood and feeling in a manner so as to provide a desirable sense of euphoria, often referred to as a "high", which is disconnected to the therapeutic ameliorative effects of the dosage form. This euphoria is found by some individuals to be psychologically and somatically desirable. In addition, after repeated administration, some users develop a craving for re-administration of the opioid. The intensity of this craving may range from a mild desire to use the drug to a preoccupation with its procurement and use, not for its therapeutic ameliorative effects, but rather for its mood-altering effects. In the latter case, the opioid becomes the central fixation in a state commonly referred to as "drug abuse," a term used to describe the usage of any drug in a manner which deviates from approved medical or social patterns within a given society. When the drug abuse involves overwhelming involvement with the use of the drug, securing its supply, and a high tendency to relapse into drug use after its withdrawal, an "addiction" is said to have developed.

Wright, U.S. Patent Application Publication 2005/0063909; Sackler, U.S. Patent Application Publication 2003/0068392; and Mehta, U.S. Patent Application Publication 2004/0202717 describe the abuse of opioid narcotics by physical and chemical tampering.

Several attempts have been proposed to curtail abuse of opioids by pharmacological methods. The main attempts have included: (1) inclusion of aversive agents along with the active pharmaceutical ingredients, as described by the above Wright, Sackler, and Mehta applications, and (2) modification of the delivery carrier of the active pharmaceutical ingredient.

Aversive agents employed in the prior art have included opioid antagonists, emetic agents, dyes, respiratory irritants, and bittering agents. The inclusion of aversive agents elicits an undesirable physical or emotional response to tampering of the therapeutic dosage form. Inclusion of aversive agents of the prior art have several shortcomings. Aversive agents that act on the peripheral senses such as taste or smell are easily bypassable by the illicit user. Aversive agents that work via internal or central nervous system senses or receptors, such as emetic agents and drug antagonists are more effective and more difficult for the illicit user to bypass. However, these agents may be problematic for the legitimate user unless the aversive agent is formulated with the TPTA in such a way that the aversive agent is not released in a significant quantity unless the dosage form is tampered with, since for example even a small amount of a bioavailable aversive agent such as an emetic agent, may cause nausea.

A noteworthy example of a drug that undergoes both unintended and illicit tampering is that of sustained release products containing oxycodone, such as in OxyContin® (Purdue Pharma, L.P., Stamford, Conn.). When used properly, OxyContin® tablets release the active ingredient oxycodone in a controlled manner within 12 hours. This time-release mechanism permits OxyContin®, unlike the earlier immediate release oxycodone formulations, to treat serious pain for up to 12 hours. Addicts learned that by crushing the tablets, and either snorting the resulting powder, swallowing the crushed tablets, or extracting the drug from the powder and injecting the drug solution, they could get a powerful and immediate euphoric high.

The high is obtained because, upon crushing the OxyContin® tablets, the illicit user damages the tablet's extended release mechanism and, as a result, is able to obtain a burst release of the therapeutic dose of oxycodone that is intended to be delivered in the body over a 12 hour period. As a result of this illicit activity, some health care providers are fearful of prescribing such medicines due to the potential of criminal liability or investigation, and hence may not be aggressively treating patients to manage severe pain by using an opioid analgesic.

It is believed that extended release narcotics such as OxyContin®, have a much lower risk of addiction than do immediate release opioid medications. The rate and intensity at which an opioid enters the brain and binds to opioid receptors is believed to determine its euphoric effect and also its addiction potential. This explains why injecting a narcotic is believed to produce a more powerful high and is more likely to increase the risk of addiction than snorting or swallowing a similar amount of narcotic. Because OxyContin®, taken whole, provides a controlled release of oxycodone over an extended period, the high it produces is diminished, as is believed the risk of addiction. Therefore, it is of clinical importance to obtain a dosage form which reduces dose dumping by reducing the "burst" release of a therapeutic agent from a tampered dosage form.

Shaw, U.S. Pat. No. 3,980,766; Hoffmeister, U.S. Pat. No. 4,070,494; and Bastin, U.S. Pat. No. 6,309,668 describe formulations designed to prevent the injection of compositions meant for oral administration. Shaw describes the incorporation of an ingestible solid which causes a rapid increase in viscosity upon exposure to an aqueous solution thereof. Hoffmeister describes the incorporation of a non-toxic, water gelable material in an amount sufficient to render the drug resistant to aqueous extraction. Bastin describes a tablet for oral administration containing two or more layers comprising one or more drugs and one or more gelling agents within each separate layer of the tablet. The resulting tablet forms a gel when combined with the volume of water necessary to dissolve the drug. This formulation thus reduces the in vitro extractability of the drug from the tablet.

The approach of these patents, while likely effective in preventing extraction of a drug and in precluding in vitro abuse of the drug by injection, fails to address the problem of abuse of a TPTA by other than extraction of a drug from a dosage form. These patents do not address abuse by crushing and swallowing a dosage form containing the TPTA without extraction of the TPTA from the dosage form, which is a commonly reported method of abuse associated with sustained-release analgesic formulations such as OxyContin®.

Pachter, U.S. Pat. Nos. 3,773,955; and 3,966,940 describe formulations containing a combination of opioid agonists and antagonists, in which the antagonist does not block the therapeutic effect when the admixture is administered orally but prevents analgesia, euphoria or physical dependence when administered parenterally by an abuser. Gordon, U.S. Pat. No. 4,457,933 describes a method for decreasing both the oral and parenteral abuse potential of strong analgesic agents by combining an analgesic dose of the analgesic agent with an antagonist in specific, relatively narrow ratios. Kaiko, U.S. Pat. Nos. 6,277,384; 6,375,957; and 6,475,494 describe oral dosage forms including a combination of an orally active opioid agonist and an orally active opioid antagonist in a ratio that, when delivered orally, is analgesically effective but that is aversive in a physically dependent subject. While such a formulation may be successful in deterring abuse, it also has the potential to produce adverse effects in legitimate patients via leaching of antagonist from the dosage form when taken as intended.

Combinations of unloaded resins and drug-resin combinations have been disclosed as they relate to modifying the release of a therapeutic agent. Hughes, U.S. Patent Application Publication 2002/0176842, describes the combination of unloaded ion exchange resins and an ionizable active ingredient in order to control drug release. Hughes, U.S. Patent Application Publication 2002/0146384 describes the use of a drug-loaded resin (resinate) and unloaded resin to modify drug release rates from dosage forms. The Hughes patent applications deal with the problem of modifying release of a drug from an intact dosage form over an extended time and do not address or relate to the problem of reducing drug abuse by tampering with dosage forms containing a TPTA.

Present methods of attempting to reduce abuse of dosage forms focus on preventing extraction of a TPTA from the dosage form in vitro. This approach works well to inhibit the abuse of a drug by an abuser who extracts the drug from a dosage form and then injects, snorts, or swallows the extracted drug separately from the dosage form. However, this approach does not address the problem of an abuser who physically tampers with a dosage form and then swallows the tampered dosage form. Therefore, a significant need remains unfulfilled to provide a dosage form that reduces or eliminates the potential for abuse of a drug by physically tampering with the dosage form containing the drug and then administering the tampered dosage unit by a route in which the untampered dosage form is intended to be administered.

DESCRIPTION OF THE INVENTION

Figure 1:
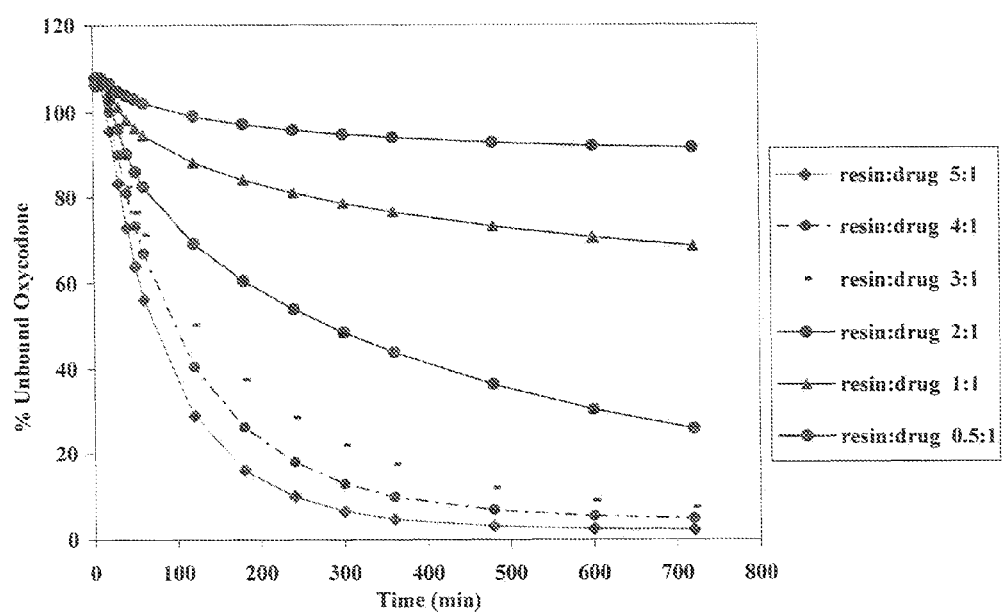
FIG. 1 is a line graph showing the percentage of unbound oxycodone in an aqueous loading solution with a varying amount of ion exchange resin Amberlite IR-69F during the drug loading process.

It has been discovered that the inclusion of a TPTA trap as part of a dosage form containing a drug, such as a TPTA, is effective in reducing or eliminating a burst release of the drug from the dosage form when the dosage form is physically tampered. The TPTA trap and the drug, such as the TPTA, may be in physical association as part of the dosage form or they may exist as separate and distinct elements of the dosage form. Because the rapid release of the drug, often referred to as "dose dumping" or "burst release," is reduced or retarded from the tampered dosage form, the invention reduces or eliminates the sensation of euphoria that would otherwise be obtained by an individual who illicitly tampers with the dosage form in order to abuse the drug. Additionally, the invention reduces or eliminates the possibility that one who unintentionally tampers with a dosage form will receive a toxic overdose of a drug. Thus, for example, the invention reduces the likelihood that an elderly individual who has difficulty in swallowing a tablet or capsule, and who breaks the tablet or capsule in order to obtain smaller particles that are easier to ingest, will receive a toxic overdose of the drug. In this way, the elderly patient is protected from being poisoned by a rapid release of the drug from the dosage form.

In one embodiment, the invention is a composition which is a dosage form that contains a drug, such as a TPTA, and a TPTA trap. The TPTA trap and the drug may be in physical association as part of the dosage form or they may exist as separate and distinct elements of the dosage form. The dosage form of the invention provides a release of drug intended by the manufacturer of the dosage form when administered in an untampered form. However, when the dosage form is tampered with, burst release of the drug from the dosage form is retarded or reduced, as compared to that from a similar dosage form not containing the TPTA trap.

In another embodiment, the invention is a method for making a dosage form. In accordance with this embodiment of the invention, a drug is combined with a TPTA trap, either as one subunit or as separate drug and TPTA trap subunits, to obtain a dosage form from which the release rate of the drug from the dosage form is not significantly impeded by the presence of the TPTA trap if the dosage form has not been tampered with, but from which a burst release of the drug from the dosage form is reduced or retarded if the dosage form has been tampered with.

In another embodiment, the invention is a method for reducing or retarding burst release of a drug from a dosage form that has been tampered with. According to this embodiment of the invention, a TPTA trap is combined with a dosage form containing a drug, wherein the TPTA trap does not significantly impede release of the drug from the dosage form when the dosage form has not been tampered with and is administered in a manner intended by the manufacturer but which TPTA trap reduces or retards burst release of the drug from the dosage form if the dosage form has been physically tampered with.

In another embodiment, the invention is a method for administering a drug. In accordance with this embodiment of the invention, a dosage form containing a TPTA trap and a drug is administered to an individual in need of the drug, wherein the TPTA trap does not significantly impede the rate of release of the drug from the dosage form when the dosage form has not been tampered with but retards or reduces a burst release of the drug from the dosage form if the dosage form has been tampered with.

As used herein, the term "tampering" means physical modification of a dosage form prior to or during administration of the dosage form. Examples of methods of tampering include chewing, grinding, and crushing, with or without the aid of a mechanical device.

As used herein, the term "burst release" is synonymous with the term "dose dumping" and means the increased percent or amount release of a drug from a dosage form within a given time interval compared with that from a dosage form that is administered in an untampered form and in a manner intended by the manufacturer of the dosage form. The percent or amount of a drug released per unit time is also referred to as "rate of release" of the drug. Burst release typically occurs from dosage forms that have been tampered with, especially from extended-release dosage forms that have been tampered with. The duration of the time of the burst may be any time interval, such as from 1 second to 2 minutes, from 2 minutes to 20 minutes, or from 20 minutes to 60 minutes or more, from the initiation of release of drug from the dosage form.

As used herein, the term "TPTA" means a tamper-prone therapeutic agent. A TPTA is a drug that has an effect on a user to which the drug is administered which effect is unintended by the manufacturer of the drug when a dosage form containing the drug has been tampered with resulting in an increase in the rate of release of the drug.

Examples of a TPTA include CNS depressants such as barbiturates and natural or synthetic opioids like morphine, oxycodone, hydrocodone, and codeine; anxiolytic agents such as benzodiazepene drugs; stimulants such as amphetamines; and locally acting anesthetic agents such as cocaine and lidocaine. Other examples of a TPTA include cardiovascular drugs, respiratory drugs, sympathomimetic drugs, cholinomimetic drugs, adrenergic drugs, antimuscarinic and antispasmodic drugs, skeletal muscle relaxants, diuretic drugs, anti-migraine drugs, anesthetics, sedatives and hypnotics, antiepileptics, psychopharmacologic agents, antipyretics, CNS stimulants, antineoplastic and immunosuppressive drugs, antimicrobial drugs, antihistamines, anti-inflammatories, antibiotics, decongestants, cough suppressants, and expectorants. Analgesics, including opioid and non-opioid analgesics, are an important class of TPTA. Examples of analgesic TPTA include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethyl-thiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacyl-morphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phena-doxone, phenomorphan, phenazocine, phenoperidine, piminodine, piritramide, propheptazine, promedol, properidine, propoxyphene, sufentanil, tilidine, and tramadol.

As used herein, the term "TPTA trap" means one or more agents that resides in or on a dosage form containing a drug, such as a TPTA, and that does not significantly impede release of the drug from the dosage form when the dosage form is administered in an untampered form and in a manner intended by the manufacturer of the dosage form but that retards or reduces burst release of the drug from the dosage form when the dosage form has been tampered with. TPTA traps are discussed in more detail below.

As used herein, the term "does not significantly impede release of a drug from a dosage form" in relation to a TPTA trap means that the rate of release of the drug from the dosage form with a TPTA trap is similar to that from a dosage form without a TPTA trap. Upon administration as intended by the manufacturer of the dosage form, with or without the TPTA trap, the release rate of the drug from the dosage form is as intended by the manufacturer of the dosage form.

The dosage form of the invention may be any dosage form by which a drug, such as a TPTA, may be administered to an individual in order to achieve a desired pharmacological effect in that individual. The dosage form may be an oral dosage form, such as a tablet, a capsule containing a plurality of particles such as granules, a hard or soft-gel capsule containing a liquid or gel, a troche, a lozenge, a sachet, a liquid or a powder. The dosage form may be an injectable dosage form, such as for intravenous, intramuscular, subcutaneous, or other parenteral routes. The dosage form may be a topical formulation, such as a topical solution or emulsion, including creams, ointments, and lotions. The dosage form may be a suppository, such as for anal or vaginal administration.

The dosage form of the invention may be one that provides immediate release of the drug when administered in the manner intended by the manufacturer or may be one that allows for controlled release of the drug. Because the danger of abuse of a TPTA due to illicit tampering of a dosage form containing the TPTA, or of accidental overdose of a TPTA due to unintentional tampering of the dosage form, is highest with controlled release dosage forms, in a preferred embodiment, the dosage form of the invention is one that allows for controlled release of a TPTA.

The drug suitable for the invention is any drug that can be administered to an individual in order to obtain a desired biochemical or pharmacological effect in the individual. Preferably, the drug is a TPTA. The invention is described herein primarily in reference to a TPTA. However, it is to be understood that the invention is applicable to any drug, even those drugs that are not within the definition of a TPTA.

The TPTA within the dosage form of the invention may be in the form of a multiplicity of subunits. Examples of subunits include particles, granules, microcapsules, microtablets, spheroids, beads, and rods. The subunits may or may not be individually or collectively covered with a coating composition which acts as a barrier or which modifies the release rate of the TPTA. Such coatings are typically made of one or more film-forming polymers. Examples of such polymers include acrylic polymers, cellulosic polymers, polylactic acid polymers, polyglycolic acid polymers, and co-polymers of polylactic and polyglycolic acid.

The TPTA of the dosage form may be free within the dosage form or may be in association with a material to form a TPTA composition. As used herein, the term "TPTA composition" refers to a physical or chemical association of a drug, such as a TPTA, with a material in a dosage form. As examples, the association of the drug with the material may be a distribution of the drug upon or within the material or an interaction or complexation of a drug with a material.

For example, a TPTA may be distributed upon or within a matrix, which may be a multiparticulate or layered matrix. The TPTA composition, such as a matrix, may or may not be in the form of a multiplicity of subunits, which subunits may be in the form of particles, granules, microcapsules, microtablets, spheroids, beads, and rods. The TPTA composition may be in the form of one or more layers, such as within a solid tablet. The TPTA composition, such as the matrix or the matrix-containing subunits or the one or more layers, may be individually or collectively covered with a coating composition. Coatings for control and release modification of TPTA are known in the art.

The TPTA of the dosage form may be associated with an ion exchange material, such as a resin. An ion exchange material may be used in combination with a TPTA that is able to interact with the ion exchange material to form a complex wherein the drug is associated with the surface of the ion exchange material or is otherwise bound to the ion exchange material. If the ion exchange material is a resin, the complex may be referred to as a resinate. The TPTA is released from the complex into a release medium upon exposure to certain ionic conditions, such as acidic or alkaline pH.

A TPTA that may be used in combination with an ion exchange material is one that exists in an ionic form, or that has one or more ionic functional groups, when in a semi-polar or polar solvent such as water. In the case of a TPTA that is not in an ionic form, the TPTA may be adsorbed or coated onto a resin. The ionized TPTA may be cationic or anionic. The TPTA may be non-ionic within the dosage form but become ionic when placed in an environment, such as acidic or alkaline pH, that causes the non-ionic drug or a functional group of the TPTA to ionize. For example, the low pH of gastric fluid may cause a TPTA, or its functional group, to ionize and become positively charged.

Ion exchange materials, such as resins, that may be used in accordance with the invention are those that are capable of associating with a TPTA of the invention to form a complex, such as a resinate, and that release the TPTA into a release medium when the complex is exposed to the release medium. Ion exchange materials that are suitable for the invention include any ion exchange material that is not toxic to animals such as humans, does not interfere substantially with the medicinal effect of a TPTA associated with the ion exchange material, contains a pharmacologically inert matrix containing functional groups that are ionic or that are ionizable under certain conditions of pH, have a moisture content between 0% and the water retention capacity of the ion exchange material, and is minimally soluble or preferably insoluble in water. The ion exchange material, such as a resin; may be a macroporous or gel type resin. In general, ion exchange materials such as resins that are suitable for use in ion exchange chromatography or for applications such as deionization of water are suitable as the ion exchange material of the invention. Ion exchange materials, including resins, are described in H. F. Walton in "Principles of Ion Exchange" (pp. 312-343) and "Techniques and Applications of Ion-Exchange Chromatography" (pp. 344-361) in Chromatography. (E. Heftmann, editor), Van Nostrand Reinhold Company, New York (1975); Kitagawa, U.S. Pat. No. 6,218,440; Barby, U.S. Pat. No. 4,522,953; Dowex: Ion exchange Resins. Fundamentals of Ion Exchange (2000); and Hughes, Ion Exchange Resins; Unique Solutions to Formulation Problems, Pharmaceutical Technology: Excipients and Solid Dosage Forms, pages 20-25 (June 2004). Examples of ion exchange materials that are other than resins are described in Hollenbeck, U.S. Patent Publication No. 2005/0013792. Other ion exchange materials, such as cross-linked sodium carboxymethylcellulose and carbomers, such as sold under the tradename Carbopol® (Noveon Inc., Cleveland, Ohio), may also be used. Additional examples of ion exchange materials that are other than resins are disclosed in Hollenbeck, U.S. Patent Publication No. 2005/0013792.

The ion exchange material or resin may be in an ionized form, a salt form, or a partial salt form, and may be cationic or anionic. In general, a cationic ion exchange material is employed with a TPTA that can be positively charged and an anionic ion exchange material is employed with a TPTA that can be negatively charged.

Examples of preferred anionic exchange resins include, but are not limited to, styrenic strongly basic anion exchange resins with a quaternary amine functionality; styrenic weakly basic anion exchange resins with a primary, secondary, or tertiary amine functionality; acrylic or methacrylic strongly basic anion exchange resins with a quaternary amine functionality; acrylic or methacrylic weakly basic anion exchange resins with a primary, secondary, or tertiary amine functionality; and allylic, and vinylic weakly basic anion exchange resins with a primary, secondary, or tertiary amine functionality.

Examples of preferred cationic exchange resins include, but are not limited to, styrenic strongly acidic cation exchange resins with sulfonic or phosphonic acid functionality; styrenic weakly acidic cation exchange resins with carboxylic or phenolic acid functionality; and acrylic or methacrylic weakly acidic cation exchange resins with a carboxylic or phenolic acid functionality.

The TPTA may be associated with a polymer other than an ion exchange material. For example, the TPTA may be in association with a high internal phase emulsion (HIPE) polymer, such as those described in Kitagawa, U.S. Pat. No. 6,048,908. Alternatively, the TPTA may be associated with a non-polymeric material. An example of a suitable non-polymeric matrix is disclosed in Tipton, U.S. Pat. No. 5,747,058.

The selection of a material with which the TPTA is associated in the dosage form to form a TPTA composition will depend on numerous factors, including the nature of the TPTA, the nature of the TPTA trap, and the release objectives that the formulator of the dosage form desires to achieve. Similarly, the method utilized for associating a TPTA with a matrix, an ion exchange material, or other polymeric or non-polymeric may be by any method known for creating such TPTA associations. An example of methods for making such matrices is disclosed in Arkenau, U.S. Patent Publication No. 2005/0236741. Other examples of methods for making TPTA associations are disclosed in Chien, Novel Drug Delivery Systems, 2d. Ed., ISBN 0824785207, Marcel Dekker Inc. (1991)

A resinate of a TPTA and an ion exchange resin may be made by mixing a TPTA in solution or suspension with an ion exchange resin at a temperature and for a time sufficient for the TPTA and the ion exchange resin to associate and form the resinate. The resinate may be left in the suspension, for example if the complex is to remain uncoated and is to be used in a liquid dosage form. Alternatively, the resinate may be filtered and dried or partially dried. The obtained resinate may then be removed and coated, if desired, such as to modulate the release rate of the TPTA loaded onto the ion exchange resin.

The TPTA trap of the dosage form of the invention may be one or more of a cushioning agent, a blocking agent, or a competitive agent. A drug, such as a TPTA, may be combined or mixed with the TPTA trap as one unit, layer, or as multiple units or layers, or may be separate from the TPTA trap as distinct units or layers. A dosage form may contain one or more TPTA traps that are cushioning, blocking, or competitive agents. An individual TPTA trap may have the properties of one or more of a cushioning, blocking, or competitive agent. For example, an alginate material may be a blocking agent due to its tackiness and a competitive agent due to the nature of its available TPTA binding functional groups. Other examples of materials that may be both cushioning and blocking agents are rosin resins and rosin resin derivatives, terpene resins and terpene resin derivatives, citric acid esters, and sucrose resins and sucrose esters.

In one embodiment, the TPTA trap is a cushioning agent. As used herein, the term "cushioning agent" refers to a material that interferes with an external mechanical force that is applied to a dosage form and which, in the absence of the cushioning agent, would cause fracturing of a TPTA composition. The cushioning agent TPTA trap is softer and/or more elastic than the TPTA composition. Examples of such "cushioning" TPTA traps include waxes or wax-like materials, elastomeric masticatory substances, rosin resins or rosin resin derivatives, terpene resins or terpene resin derivatives, pH dissolution dependent polymers, and ethyl cellulose or cellulose derivatives such as cellulose esters. The cushioning agent TPTA trap may be one or more materials that act as a cushioning trap or may be a combination of materials which alone do not act as a cushioning trap but which, when combined, act as a cushioning trap.

Waxes or wax-like substances are hydrophobic or water-insoluble materials that are solid at room temperature and have a melting point between 30° C. and 300° C. Examples of suitable waxes and wax-like substances include beeswax, glycowax, castor wax, carnauba wax, candelilla, paraffin, microcrystalline wax, ozokorite, ceresin, geniune japan wax, and montan.

Suitable elastomeric masticatory substances utilized in the present invention include both natural and synthetic masticatory substances. Examples of suitable elastomeric masticatory substances (coagulated or concentrated lattices) of vegetable origin include chicle, chiquibul, crown gum, gutta hang kang, massaranduba balata (and the solvent-free resin extract of massaranduba balata), massaranduba chocolate, nispero, rosidinha (rosadinba), Venezuelan chicle, jelutong, leche caspi (sorva), pendare, perillo, leche de vaca, niger gutta, tunu (tuno), chite, and natural rubber (smoked sheet and latex hevea brasiliensis solids), corn zein, and biodegradable prolamine compositions such as described in U.S. Pat. No. 6,858,238. Other examples of suitable elastomeric masticatory substances include butadiene-styrene rubber, isobutylene-isoprene copolymer (butyl rubber), paraffin, petroleum wax, petroleum wax synthetic, polyethylene, polyisobutylene, polyvinyl acetate, and polyvinyl alcohol.

Examples of rosin resin and rosin resin derivatives include glycerol ester of partially dimerized rosin, glycerol ester of partially hydrogenated gum or wood rosin, glycerol ester of polymerized rosin, glycerol ester of gum rosin, glycerol ester of tall oil rosin, glycerol ester of wood rosin, lanolin methyl ester of partially hydrogenated rosin, pentaerythritol ester of partially hydrogenated gum or wood rosin, pentaerythritol ester of gum or wood rosin. A preferred rosin resin derivative is glycerol ester of wood rosin, such as ester gum 8BG, as manufactured by Hercules Inc. (Wilmington, Del.).

Examples of terpene resin or terpene resin derivatives include natural or synthetic resins or derivatives of α-pinene, β-pinene, and dipentene. Preferred terpene resin derivatives are sold under the tradename Piccolyte® (Hercules Inc., Wilmington, Del.).

Examples of polymers whose dissolution is pH dependent include cellulose acetate phthalate, polyvinylacetate phthalate (enteric polymers), and Eudragit® polymers (Rohm GmbH & Co., Damrstadt, Germany). These polymers may be coated onto a TPTA composition such as a resinate, which coating may be a combination of the polymer with a suitable plasticizer or blends of plasticizers, and act as cushioning agents due to their elastic nature. They dissolve at particular locations within the gastrointestinal tract (GIT) because of the unique pH at the particular location in the GIT. For example Eudragit E is an acid soluble polymer that dissolves at pH of 5.0 or less, such as is present in the stomach. In contrast, Eudragit L, cellulose acetate phthalate, and polyvinylacetate phthalate dissolve at pH of 6.0 or higher and Eudragit S dissolves at pH of 7.0 or higher, which pH levels are typically found in the small and large intestines. After the Eudragit polymer is dissolved, the TPTA composition complex is then exposed to the gastrointestinal fluid, whereby the TPTA is then released.

Examples of cellulose derivatives other than ethyl cellulose that may be used as cushioning agents include cellulose acetate (CA), cellulose acetate butyrate (CAB), and cellulose acetate propionate (CAP).

In one embodiment, the TPTA trap is a blocking agent. As used herein, the term "blocking agent" refers to a material that blocks or reduces release of a TPTA from a TPTA composition or from a dosage form when a dosage form, which may or may not contain a TPTA composition, is exposed to a dissolution medium. The blocking agent TPTA trap may coat, agglomerate, decrease the exposed surface of, or increase the hydrophobicity of the TPTA composition, thereby retarding or reducing the release of TPTA from the TPTA composition when exposed to a dissolution medium. Blocking agent TPTA traps may be composed of materials that are tacky, gelling, hydrophobic, water-impermeable, or of limited water solubility. The blocking agent TPTA trap may be one or more materials that acts as a blocking trap or may be a combination of materials which alone do not act as a blocking trap but which, when combined, act as a blocking trap.

A tampered dosage form with a blocking type of TPTA trap is analogous to an insect that is imbedded in amber. The amber presents a tacky thick hydrophobic medium that constrains movement of the insect. Similarly, the blocking TPTA trap may present a medium that blocks, reduces or retards access of unbound ions in the medium to binding sites on the ion exchange material or blocks, reduces or retards TPTA release from a TPTA composition when the composition is tampered with. Examples of such "blocking" TPTA traps include polymers of acrylic acid crosslinked with allyl sucrose or allylpentaerythritol, acrylic polymers, neutral glucans, a hydrocolloid or mixture of hydrocolloids, citric acid esters (CAE) such as those disclosed in Shukla, U.S. Patent Publication No. 2005/0266083, or sucrose resins such as disclosed in Tipton, U.S. Pat. No. 5,737,058.

Examples of polymers of acrylic acid crosslinked with allyl sucrose or allylpentaerythritol include Carbopol® copolymers, such as those made by Noveon Inc. (Akron, Ohio).

Examples of acrylic polymers include methacrylic polymers, acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), glycidyl methacrylate copolymers, and combinations thereof. An example of a suitable acrylic resin is ammonio methacrylate copolymer NF21, a water-insoluble copolymer of ethyl acrylate, methyl methacrylate, and trimethylammoniumethyl methacrylate chloride. This polymer is manufactured by Rohm Pharma GmbH (Darmstadt, Germany), and sold under the tradename Eudragit®. Eudragit® RS30D is preferred.

Examples of neutral glycans include pullulan, amylose, dextran, and cellulose.

Examples of hydrocolloids are those that are derived from seaweeds, seed gum, plant exudates, fiber extracts, biosynthetic gums, gelatins, biosynthetic process starch or cellulosic materials, alginates, sodium alginate, calcium alginate, carrageenans, guar gum, locust gum, tars gum, gum arabic, ghatti gum, agar gum, xanthan gum, and pectin.

Examples of citric acid esters include triethyl citrate (TEC), acetyl triethyl citrate (ATEC), tributyl citrate (TBC), acetyl tributyl citrate (ATBC), acetyltri-n-hexyl citrate (A-6), and butyryltri-triethyl n-hexyl citrate (B-6).

Examples of sucrose resins and sucrose esters include sucrose acetate isobutyrate (SAIB) and its derivatives.

In one embodiment, the TPTA trap is a competitive agent. As used herein, the term "competitive agent" refers to a material that associates with the ionic form of a drug, such as a TPTA, or with the ionic binding sites of an ion exchange material. Such TPTA traps are ionically accommodating. That is, the network of the TPTA trap associates with the functional groups of the TPTA or the ionic functional groups of the ion exchange material, such as a resin, with which the TPTA is complexed. The association of the competitive agent TPTA trap and a TPTA or the ionic binding sites of an ion exchange material may be accomplished by any mode of molecular recognition or inclusion including, but not limited to, ionic interactions, metal ion-ligand interactions, hydrogen bonding and other dipole-dipole interactions, interpenetration by solvent swelling, covalent attachment, hydrophilic interactions, hydrophobic interactions including .pi.-.pi. stacking interactions, or any combination thereof. The competitive agent TPTA trap may be one or more materials that acts as a competitive trap or may be a combination of materials which alone to not act as a competitive trap but which, when combined, act as a cushioning trap.

An example of a competitive agent TPTA trap is a polyelectrolyte hydrogel or a complex or coacervate of polyelectrolyte hydrogels. A coacervate is a complexation between two oppositely charged polyelectrolytes that can lead to precipitation (insoluble solid phase), coacervate formation (dense liquid phase), soluble complexes. The coacervate is formed through initial rapid coulombic bonding, formation of new bonds/restructuring of chain distortions and aggregation of secondary complexes. The polyelectrolyte hydrogels may be anionic or cationic in nature. Examples of suitable hydrogels include poly(HEMA-co AA) (hydroxyethyl methacrylate-co acrylic acid) covalent hydrogel, carboxymethylcellulose, alginate, dextran sulfate, carboxymethyl detran, heparin, carrageenan, pectin, xanthan, chitosan, polyethyleneimine, poly(4-vinyl-N-butylpyridinium) bromide, quarternized polycations, and poly(vinylbenzyltrimethyl) ammonium hydroxide.

Another example of a competitive agent TPTA trap is an ion exchange material, such as a resin, that is not complexed to the TPTA in the dosage form and that is barrier coated with a water impermeable coating so as not to have any binding sites exposed or to be active if the system is utilized as intended by the manufacturer. However, when activated via physical tampering, the ion exchange resin trap serves to act as a depot for the temporary complexation of therapeutic ingredient and subsequently reduce the amount of therapeutic agent which is immediately available in vitro or in vivo.

The TPTA trap, whether a cushioning, blocking, or competitive agent, is preferably water-insoluble, or at least sparingly water-soluble, or has a pH dependent solubility. If the TPTA trap is readily water soluble, it might be possible for an individual to mechanically tamper with a dosage form by crushing the dosage form in water, which would permit the TPTA trap to be dissolved rapidly in the water and thereby separated from the remaining portion of the dosage form. In contrast, if the TPTA trap has low water solubility, the TPTA and TPTA composition would remain in association with the TPTA trap, even if the dosage form is situated in an aqueous medium.

When using certain TPTA traps, it may be desirable or necessary to include in the dosage form a TPTA trap activator. For a TPTA trap that requires an activator in order to function as a TPTA trap, the combination of the TPTA trap and the activator may be considered to be a TPTA trap or a TPTA trap system. An activator is a substance that increases the effectiveness of a TPTA trap or that works in conjunction with a TPTA trap to decrease the possibility of dose dumping when a dosage form is physically tampered. The amount of TPTA trap, and of an activator, present in the dosage form is that which is sufficient to achieve its purpose and will be formulation dependent.

The activator may interact with a TPTA trap when a dosage form is tampered to change the form of the TPTA trap from an inactive form to one that is capable of reducing or retarding dose dumping from the dosage form. An example of this type of activator is water, which may be encapsulated, such as by a coating, within an untampered dosage form or otherwise sequestered from contact with the TPTA trap. When the dosage form is physically tampered with, however, the coating is destroyed, thus permitting the water to interact with the TPTA trap, thereby converting the previously inactive TPTA trap material into an effective TPTA trap.

An example of a TPTA trap that is activated upon contact with water is a carbomer polymer powder. The carbomer polymer powder is dispersed in a dosage form and is inactive if the dosage form is not tampered with. Upon tampering with the dosage form, however, previously encapsulated water is permitted to interact with the carbomer powder, transforming it into a gel-like matrix that coats the TPTA composition and reduces dose dumping of the TPTA from the dosage form.

The TPTA trap may be one that does not require activation. Even without activation, such TPTA traps act to reduce or retard burst release of a TPTA from a tampered dosage form but do not affect release of the TPTA from the dosage form when the dosage form is administered in the intended manner. For example, a TPTA/ion exchange material complex, such as a resinate, may be mixed or coated with a thick coating prepared with one or more polymers, such as pH solubility dependent polymers, and a solvent such as triethyl citrate or acetyl triethyl citrate. The thick coating inhibits an intentional abuser from crushing and extracting the TPTA from the dosage form or improperly using the dosage form. However, when swallowed in an untampered form, the polymer of the viscous gel is dissolved within the GI tract, thereby releasing the TPTA as intended by the manufacturer.

The TPTA trap may include additional optional components that enhance its function or its characteristics. Additives such as liquid vegetable oils or plasticizers, such as citric acid esters, may be used to modulate the elastic or mechanical properties of the TPTA trap materials for better protection of the integrity of the TPTA composition upon tampering. Other additives such as citric acid esters and water soluble and water insoluble polymers such as ethyl cellulose and hydroxypropyl methyl cellulose (HPMC) may be used in conjunction with a TPTA trap to modulate the mechanical properties of the TPTA trap or to modulate the release of the loaded TPTA.

The TPTA trap in the dosage form, and the activator if present, may be in the form of a solid, a semi-solid, or a liquid. The TPTA trap may be in the same or a different form as the TPTA composition. The forms of a semi-solid or liquid trap are especially useful in capsule dosage forms, such as a soft or hard gelatin capsule. Solid forms of TPTA trap, and activator, include microcapsules, powders, and beads. Methods of preparing microcapsules, powders, and particle beads are well known in the art and include spray drying, spray chilling, rotary disk atomization, fluid bed coating, stationary nozzle coextrusion, extrusion-spheronization, hot-melt extrusion, centrifugal head coextrusion, and submerged nozzle coextrusion, phase separation, solvent evaporation, solvent extraction, interfacial polymerization, simple and complex coacervation, in-situ polymerization, and liposomal encapsulation. If desired, the TPTA trap, and activator, may be rolled into a sheet and then stamped into a mold or shape or may be compressed using a compression press method.

The dosage form may contain additional optional components that may or may not be associated with a TPTA, a TPTA composition, a TPTA trap, or a TPTA trap activator. One optional component is one or more coatings that may be on the TPTA, on the TPTA composition, on the TPTA trap, or on the TPTA trap activator. These coatings, which act as barriers or modify the release rate of the coated substance, are made of film-forming polymers such as acrylic polymers, cellulosic polymers, polylactic acid polymers, polyglycolic acid polymers, and co-polymers of polylactic and polyglycolic acid. A plasticizer, such as acetyl triethyl citrate, acetyl tributyl citrate, triethyl citrate, diethyl phthalate, dibutyl phthalate, or dibutyl sebacate may be admixed with the polymer of the coating. Coatings on the TPTA composition are preferably water permeable to permit interaction of these components of the dosage form with the fluid of the GI tract. The TPTA trap and/or the activator preferably are barrier coated so that these components will not interfere with the intended release profile from the TPTA composition unless the dosage form is tampered with. Coatings that are insoluble in the gastrointestinal tract are preferred, especially for coatings to be used for the TPTA trap and activator. In this way, the TPTA trap and activator do not function to inhibit burst release when the dosage form is administered as intended by the manufacturer, such as by swallowing the dosage form in its entirety. If desired, the dosage form may be covered with an enteric coating. Methods of making polymer coatings and of coating components of dosage forms are known in the art.

The dosage form may include additional optional components that enhance the function or characteristics of the dosage form or of the components of the dosage form, such as the TPTA trap or TPTA trap activator. Such components may include those that modify viscosity or prevents total separation of the TPTA trap components. Other components, such as preservatives, stabilizers, anti-oxidants, coloring agents, isotonic agents, lubricants, humectants, sequesterants, or oils may be added. Examples of preservatives are paraben derivatives such as methyl or propyl paraben. Examples of anti-oxidants are butyl hydroxyanisole, butyl hydroxytoluene, propyl gallate, and vitamin E acetate. An example of a humectant is sorbitol. Optional oil components of the dosage form include oils, fats, and fatty acid substances, including fatty alcohols such as lauryl, myristyl, stearyl, ceryl, or cetostearyl alcohol, fatty acids and derivatives such as fatty acid esters, fatty acid mono-, di-, or tri-glycerides, hydrogenated fats or oils, peanut oil, paraffin oil, castor oil, coconut oil, corn oil, olive oil, silicone oil, silicone oil, macrogol glycerides, and soya oil.

If desired, an aversive agent or a TPTA antagonist may be included within the dosage form, such as by complexing or including the aversive agent with the TPTA trap. Such aversive agents include capsaicin or emetics, or other noxious materials that elicit an unpleasant reaction in a user if the TPTA of the dosage form is administered after being tampered with, such as antagonist to the drug contained in the dosage form, an emetic agent, a dye, a respiratory irritant, and a bittering agent. Examples of suitable aversive agents are disclosed in Chang, U.S. Patent Publication No. 2004/0228802, in Hughes, U.S. Patent Publication No. 2003/0068276, and in Wright, U.S. Patent Publication No. 2005/0063909. If the aversive agent is an antagonist, the nature of the antagonist will depend on the identity of the TPTA in the dosage form. If an aversive agent or antagonist is included in the dosage form, it is preferred that such aversive agent or antagonist be coated so that it will not be released to provide its aversive effect when the dosage form is administered in the manner in which it is intended. The aversive agent, such as an antagonist, may be combined with a TPTA trap, such as ester gum or terpene resin derivative or complexed with an ion exchange resin, and coated so that it will be sequestered unless the exchange trap is activated, such as by tampering with the dosage form. In this way, the aversive agent will not affect the therapeutic value of the dosage form if administered as intended.

The dosage form of the invention may optionally include one or more additional drugs that may or may not be in association with an ion exchange material and the release of which additional drug may or may not be affected if the dosage form is tampered. Such additional drugs may include those that are used in combination with a TPTA but which are not, in themselves, prone to being abused. An example of such an additional drug is guaifenesin, which is often used as a component of cough medications.

The invention is further described in the following non-limiting examples. In the examples, the invention is illustrated utilizing oxycodone. One skilled in the art will understand that oxycodone is a representative of the TPTA of the invention and that any drug, especially a TPTA that may cause an effect unintended by the manufacturer when tampered with, is suitable for the invention.

Example 1

Loading of TPTA onto an Ion Exchange Material

A. Washing of Resin

An appropriate amount of ion exchange resin Amberlite® IR-69F (sulfonated, divinylbenzene/styrene copolymer, Na ion form, Rohm and Haas Company, Philadelphia, Pa.) was weighed and transferred to a beaker. Sufficient volume of reverse osmosis (R/O) water was added to the beaker to cover the resin by several inches. The resin was stirred for approximately 10 minutes. The stirring was stopped to allow the resin particles to settle at the bottom of the beaker. The supernatant was decanted. This washing procedure was repeated several times until the supernatant was clear. The suspension was then filtered using a Buchner funnel. The washed and filtered resin was dried at 60° C. in an oven overnight.

B. Effect of Resin to TPTA Ratio on TPTA Bonding

Figure 2:
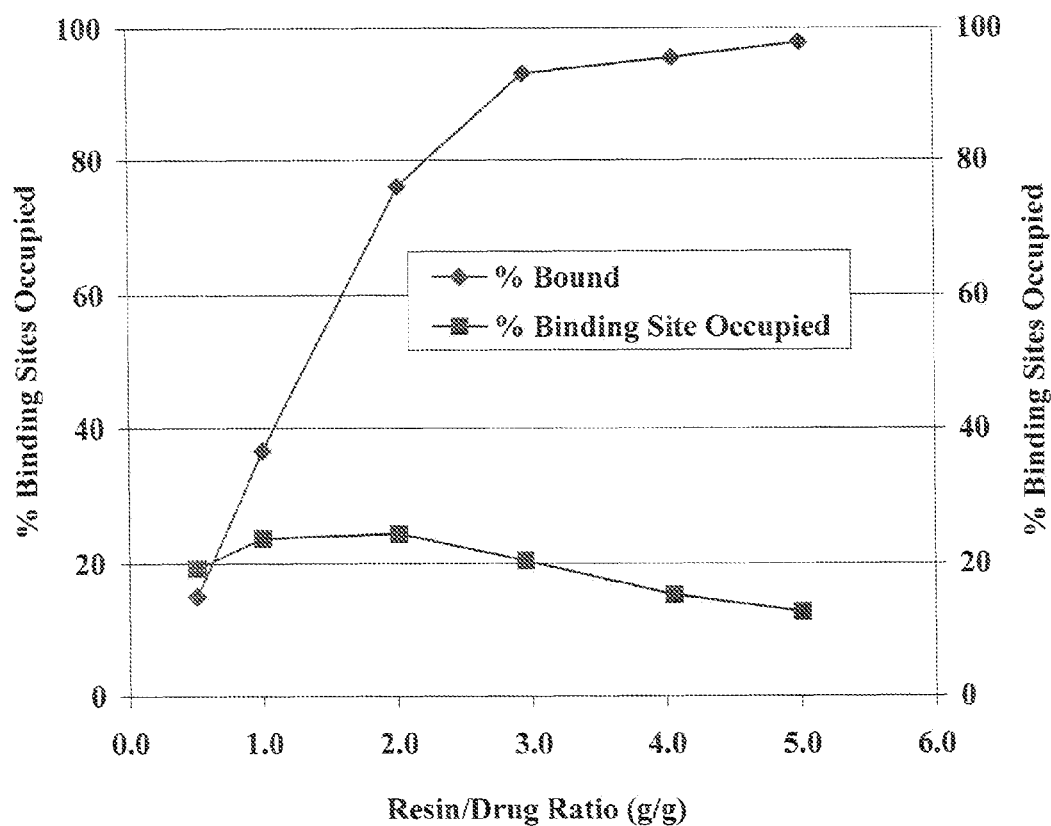
FIG. 2 is a line graph showing the effect of resin to drug ratio on the percentage of oxycodone bound onto ion exchange resin Amberlite IR-69F.

Approximately 500 mg of oxycodone hydrochloride was dissolved in 1000 ml of R/O water to obtain a stock solution. One hundred and fifty milliliters of the stock solution was added to each of 6 dissolution vessels of 150 ml capacity. Different amounts (375 mg, 300 mg, 225 mg, 150 mg, 75 mg, and 37.5 mg) of washed and dried ion exchange resins of Example 1A were added to each of the 6 dissolution vessels. The mixture was stirred at 100 rpm using a paddle at room temperature for 12 hours. The obtained TPTA-resin complex (TPTA-loaded resinate) was then filtered and copiously washed with R/O water to remove any unbound TPTA, and dried at 60° C. in an oven overnight. The percentage of unbound oxycodone in the aqueous solution was determined using a UV spectrophotometer and is shown in FIG. 1. The percentage of oxycodone bound onto the ion exchange resin and the percentage of the binding sites occupied by oxycodone were also calculated, and are shown in FIG. 2.

C. Preparation of Oxycodone Loaded Resinates with Amberlite IR-69F or IRP 69

Approximately 1.5 grams of oxycodone hydrochloride were dissolved in 200 ml of R/O water. Six grams of ion exchange resin (Amberlite® IR-69F or Amberlite® IRP 69) were added into the solution, and the mixture was stirred at 400 rpm at room temperature for 12 hours. The resultant TPTA-loaded resinates were then filtered and washed copiously with R/O water and dried at 60° C. in an oven overnight.

Example 2

Extraction of Oxycodone from TPTA Loaded Resinate

A. Extraction in an Acid Medium

Figure 3:
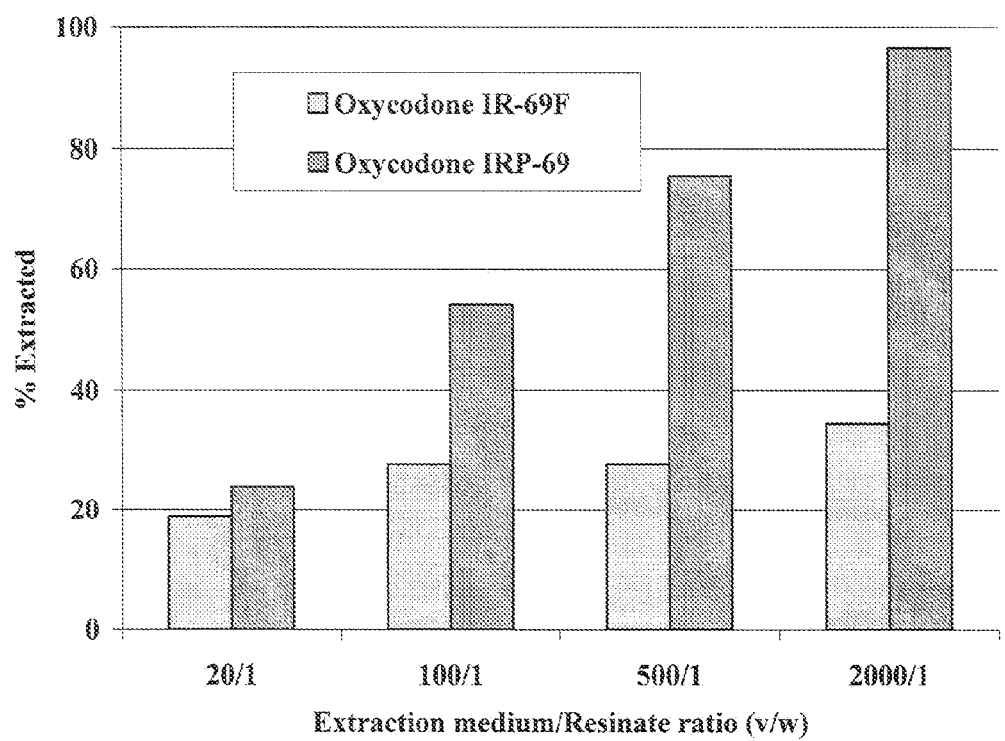
FIG. 3 is a bar graph showing the percentage of oxycodone extracted from drug-loaded resinates after being exposed to 1N HCl for 30 minutes.

An appropriate amount of the TPTA loaded resinates of Example 1C was weighed and dispersed in different volumes of 1N HCl to obtain the following ratios between dilutions of the medium and the resinate: 20/1, 100/1, 500/1, and 2000/1 (v/w). The resulting mixtures were stirred for 30 minutes. The amount of oxycodone extracted was determined using a UV spectrophotometer. The percentages of oxycodone extracted from oxycodone loaded IR-69F and IRP-69 in 1N HCl are shown in FIG. 3. As shown in FIG. 3, a much higher percentage of the TPTA was extracted from IRP-69 than from the IR-69F resinate. This is believed to be due to the smaller particle size of the IRP-69 compared to the IR-69F.

B. Extraction in 10% Saline Medium

Figure 4:
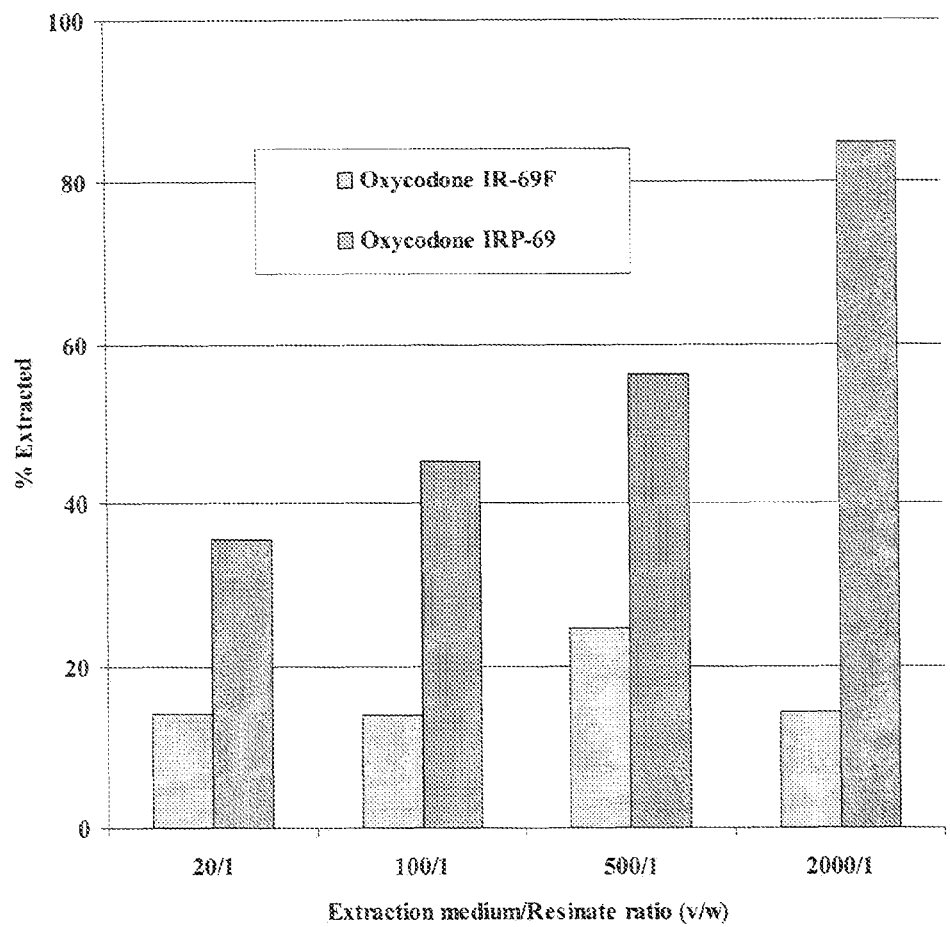
FIG. 4 is a bar graph showing the percentage of oxycodone extracted from drug-loaded resinates after being exposed to a 10% NaCl water solution for 30 minutes.

The procedure of Example 2A was repeated except that the resinates were weighed and dispersed in different volumes of 10% NaCl to obtain the following ratios between the medium and the resinate: 20/1, 100/1, 500/1, and 2000/1 (v/w). The percentages of oxycodone extracted from oxycodone loaded IR-69F and IRP-69 in 10% NaCl are shown in FIG. 4.

C. Extraction by Crushing and Dissolving in Boiling Water

Figure 5:
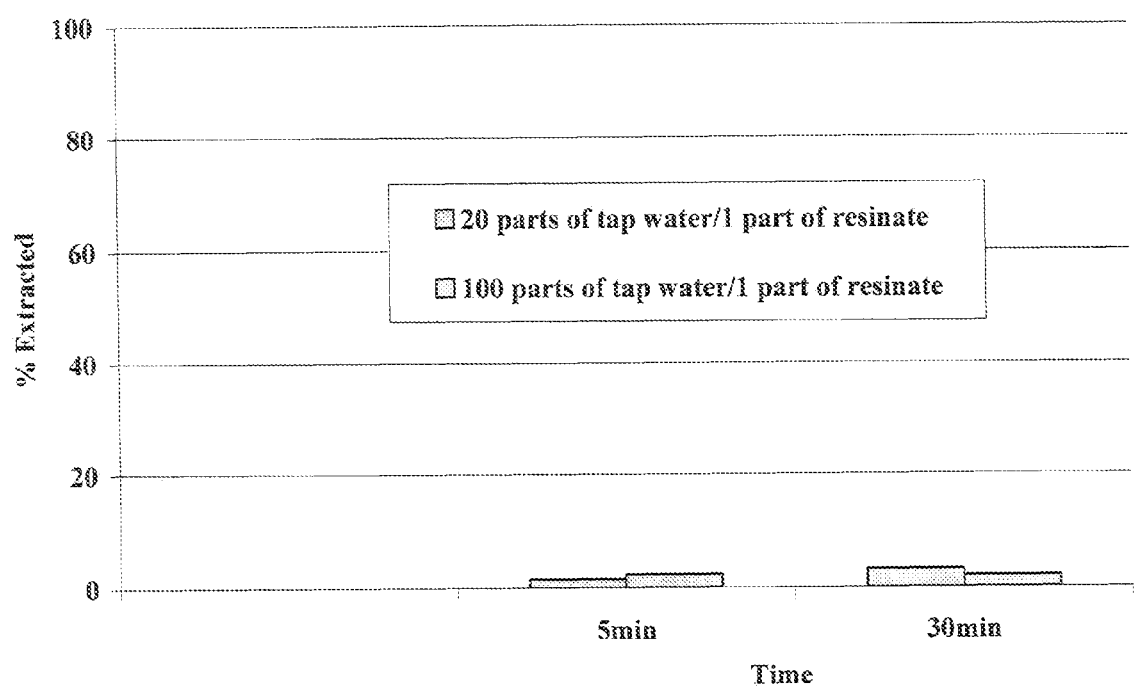
FIG. 5 is a bar graph showing the percentage of oxycodone extracted from crushed oxycodone IR-69F resinate in tap water at 100° C.

The procedure of Example 2A was repeated except that only the resin Amberlite® IR-69F was used and the resinates were first crushed and then extracted with different volumes of boiling tap water. The percentage of oxycodone extracted from the crushed oxycodone loaded IR-69F in boiling tap water is shown in FIG. 5.

D. Extraction by Crushing and Dissolving in 40% Ethanol

Figure 6:
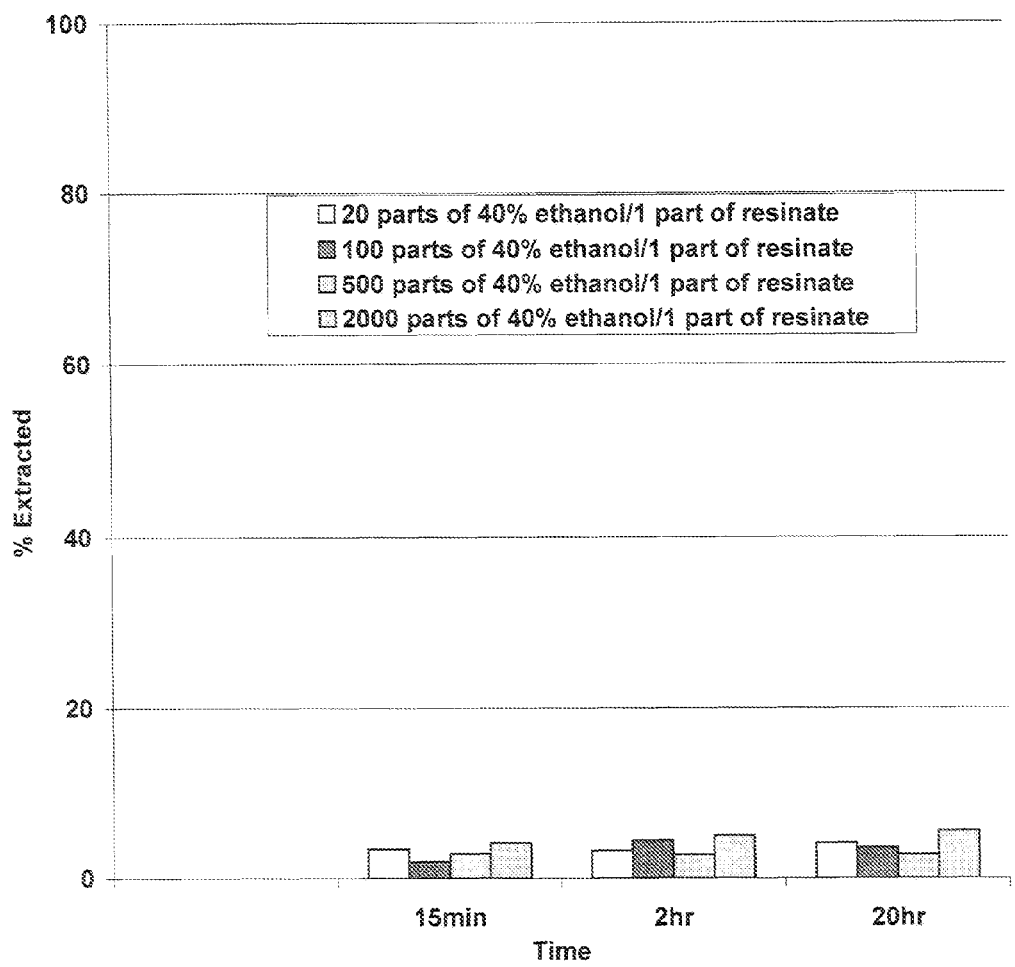
FIG. 6 is a bar graph showing the percentage of oxycodone extracted from crushed oxycodone IR-69F resinate in 40% ethanol.

The procedure of Example 2A was repeated except that only the resin Amberlite® IR-69F was used and the resinates were first crushed and then extracted over various time periods with different volumes of 40% ethanol. The percentage of oxycodone extracted from the crushed oxycodone loaded IR-69F in 40% Ethanol is shown in FIG. 6.

E. Comparison of Extraction in 2% Saline Medium Over an Extended Time Period

Figure 7:
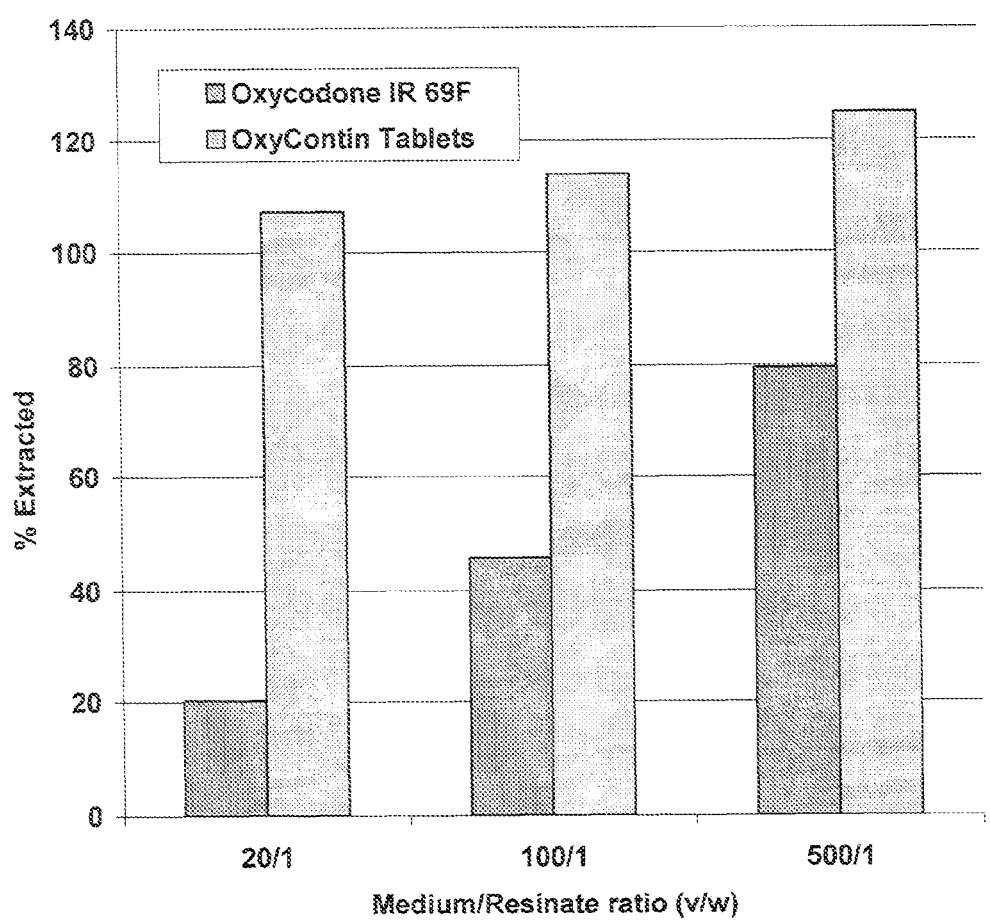
FIG. 7 is a bar graph showing the percentage of oxycodone extracted from oxycodone IR-69F resinate and OxyContin® Tablets in 2% NaCl for 22 hours.

A resinate of oxycodone and Amberlite® IR-69F resin was made and the extraction of oxycodone from the resinate by immersion in 2% NaCl for 22 hours was compared to the extraction of oxycodone from the commercial product, Oxy-Contin® tablets. FIG. 7 shows the comparison of the percentage of oxycodone extracted from Oxycodone FR-69F resinate and the commercially available OxyContin® tablets.

Example 3

Dissolution of Oxycodone from Coated and Uncoated Oxycodone IR-69F Resinates

Figure 8:
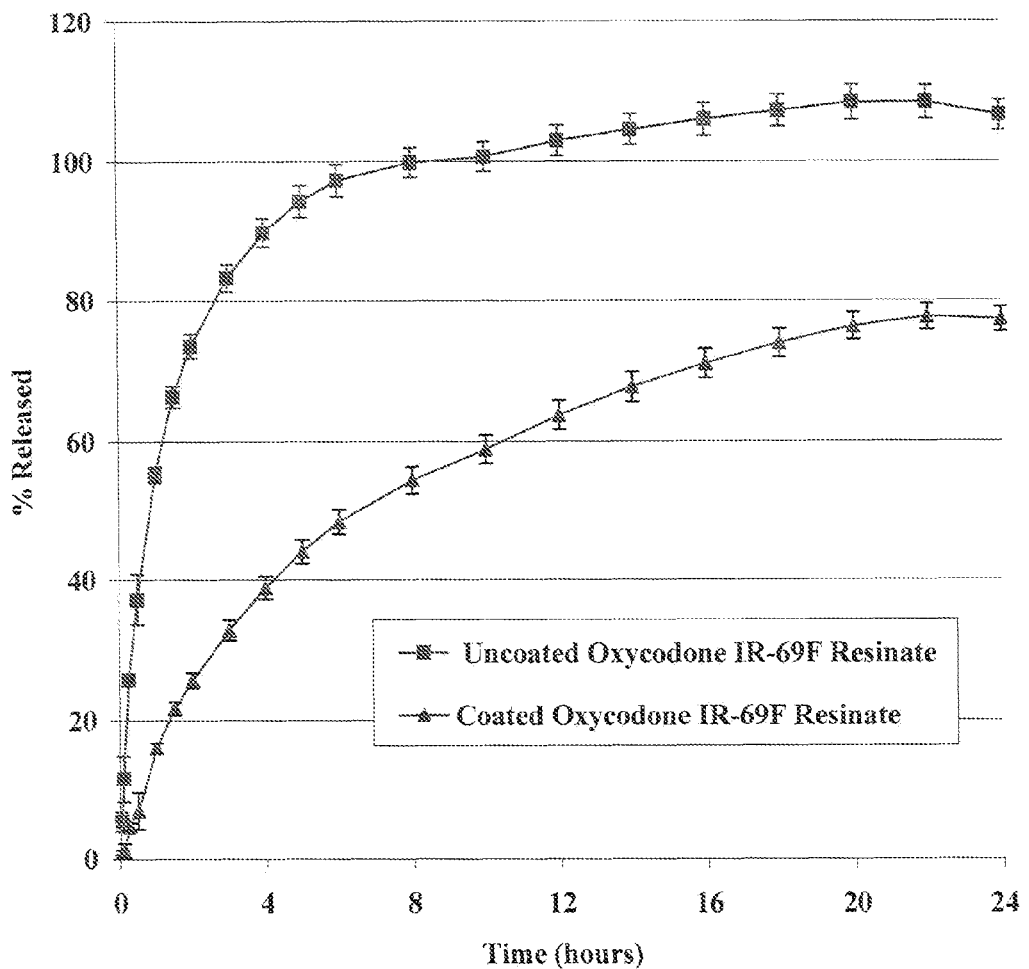
FIG. 8 is a line graph showing the release of oxycodone from uncoated and coated Oxycodone-IR-69F resinate.

Oxycodone IR-69F resinates were coated with Aquacoat® ECD ethylcellulose polymer (FMC Biopolymer, Philadelphia, Pa.) using a MiniGlatt fluid bed coater. Drug release from the coated and uncoated Oxycodone IR-69F resinate in simulated gastric fluid (SGF) was determined using USP apparatus I at 100 rpm. The percentage of drug released from the uncoated and coated Oxycodone IR-69F resinate is shown in FIG. 8. It is evident from the figure that the release of oxycodone from the coated Oxycodone IR-69F resinate is much slower than that from the uncoated drug loaded resinate, indicating that the release of the drug from IR-69F resinate may be modulated by coating these resinates.

Example 4

Use of Cellulose Acetate Butyrate as a Cushioning TPTA Trap

An oxycodone loaded TR-69F resinate was prepared using the procedure described in Example 1. A TPTA trap was prepared by the following process: approximately, 80 grams of Cellulose Acetate Butyrate 171-15 (CAB) was weighed and dispersed in 320 grams of acetyl triethyl citrate. The mixture was heated to about 160° C. and stirred until a clear viscous mass was obtained. The hot mass was poured into a container containing liquid nitrogen while vigorously stirring. An appropriate amount of starch was added when the liquid nitrogen was evaporated to prevent sticking of the resulting CAB beads (cushioning agent TPTA trap). The cushioning agent TPTA trap was obtained as discrete starch coated CAB particles.

An appropriate amount (1.6 g) of oxycodone loaded IR-69F resinate containing 320 mg of oxycodone was weighed and mixed with an appropriate amount (1.6 g) of the TPTA trap. The mixture was then crushed in using a commercially available coffee grinder. TPTA release from the uncrushed and crushed oxycodone loaded TR-69F resinate in the presence or absence of the cushioning agent TPTA trap was determined in 900 ml of simulated gastric fluid using USP Apparatus 2 at 50 rpm. The result is shown in FIG. 9.

Figure 9:
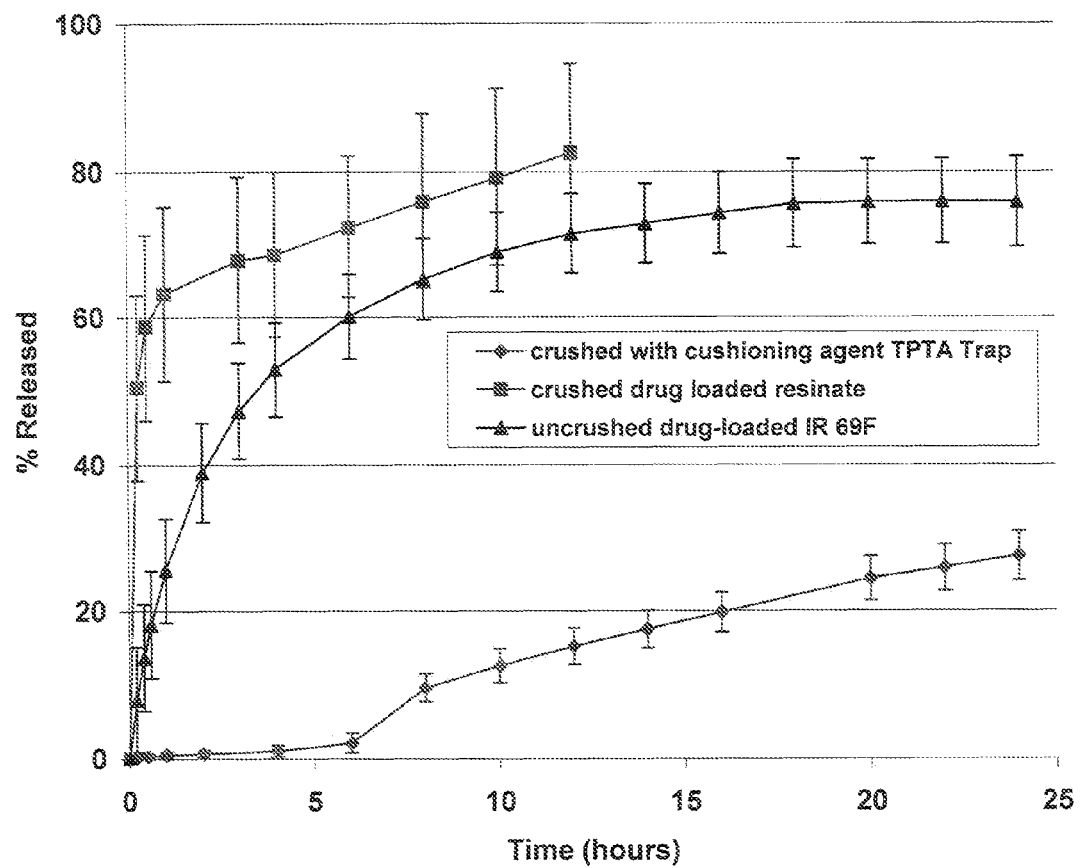
FIG. 9 is a line graph showing the dissolution profiles of oxycodone released from uncrushed and crushed oxycodone IR-69F resinate in presence or absence of a cushioning agent TPTA trap during crushing.

As shown in FIG. 9, the rate of dissolution of oxycodone from the crushed resinate in the presence of the physically activated cushioning agent TPTA, trap was markedly slower than that from a similar crushed resinate lacking the TPTA trap and was even slower than from an uncrushed resinate lacking the TPTA trap. It is conceived that this effect is due to the cushioning effect of the TPTA trap, which reduces the crushing of the resinate, and agglomerates the TPTA loaded resin beads together with the TPTA trap, indicating that the CAB also shows properties of a blocking agent TPTA trap.

Example 5

Use of an Ester Gum as a TPTA Trap

An oxycodone loaded IR-69F resinate was prepared using the procedure described in Example 1. An ion exchange resin trap was prepared by following process: approximately, 80 grams of acetyl tributyl citrate was weighed and added to 320 grams of Ester Gum 8BG glycerol ester of wood rosin (Hercules Incorporated, Wilmington, Del.). The mixture was heated to about 100° C. and stirred until a clear gel was obtained.

The ion exchange resin trap was prepared as starch coated discrete Ester Gum 8BG particles (blocking agent TPTA trap). An appropriate amount of oxycodone loaded IR-69F resinate (400 mg) containing 80 mg of oxycodone was weighed and mixed with an appropriate amount (400 mg) of the blocking agent TPTA trap. The resulting mixture was crushed with a mortar and a pestle. TPTA release from the uncrushed and crushed oxycodone loaded IR-69F resinate in the presence and absence of the blocking agent TPTA trap was determined in 900 ml of simulated gastric fluid using USP Apparatus II at 50 rpm. TPTA dissolution results are shown in FIG. 10.

Figure 10:
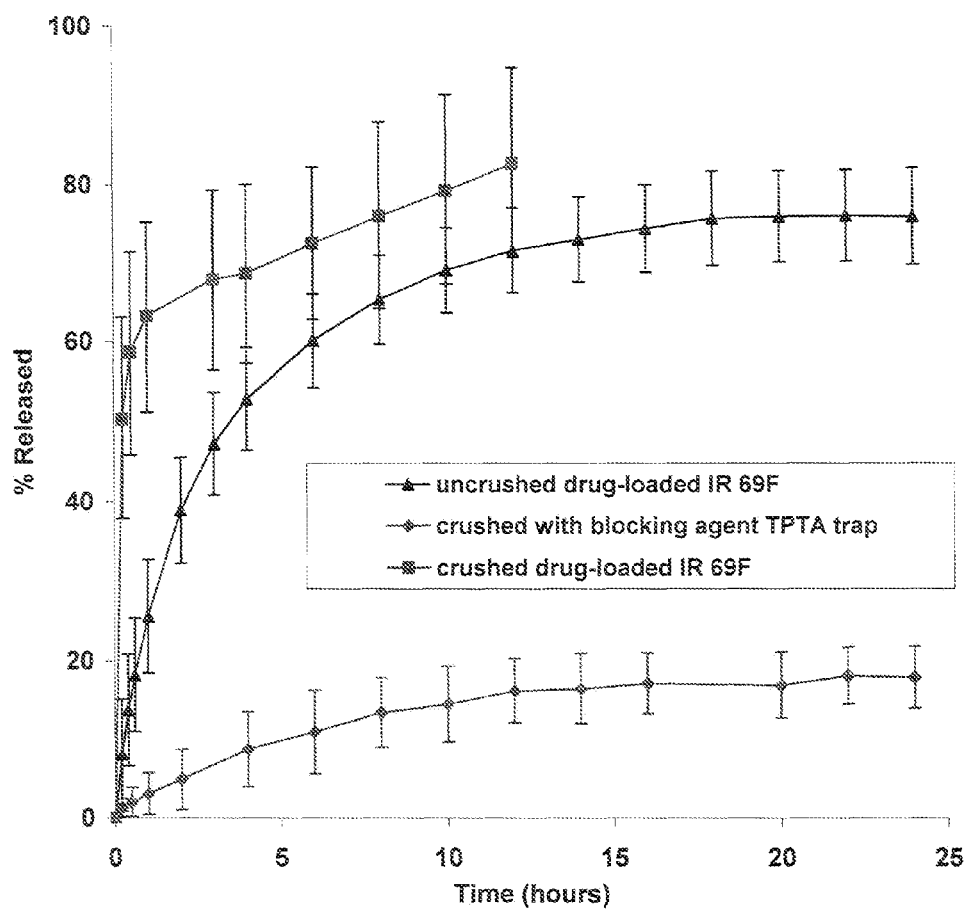
FIG. 10 is a line graph showing the dissolution profiles of oxycodone released from uncrushed and crushed oxycodone IR-69F resinate in the presence or absence of a blocking agent TPTA trap during crushing.

As shown in FIG. 10, the rate of dissolution of oxycodone from the crushed resinate in the presence of the blocking agent TPTA trap was markedly slower than that from a similar crushed resinate lacking the TPTA trap and was even slower than that from an uncrushed resinate lacking the ion exchange resin trap. It is conceived that this effect is due to the cushioning and blocking effects of the TPTA trap, which prevented the resinate from being efficiently crushed and which retarded or reduced the TPTA from accessing the dissolution medium.

Example 6

Use of a Narcotic Antagonist as a Model Aversive Agent

Naltrexone (an opioid antagonist)-loaded IR-69F resinate was prepared using similar procedures as described in Example 1. Naltrexone-loaded resinates were coated with ethylcellulose (Ethocel, 10 cp, Dow Chemical Company, Midland, Mich.) using a MiniGlatt fluid bed coater. The formula of the coating solution is shown in Table 1.

TABLE 1

| Ingredient | Concentration (% w/w) |
| --- | --- |
| Ethocel ® (10 cp) | 5.0 |
| Acetyl Tributyl Citrate (ATBC) | 1.5 |
| 2-propanol | 88.5 |
| Water | 5.0 |

The coating solution was prepared according to the following procedure. Appropriate amounts of 2-propranol and R/O water were weighed and transferred into a beaker. An appropriate amount of ethylcellulose (EC) was dispersed into 2-propanol-water mixture under continuous stirring for 10 hours. After completely dissolving the EC in the 2-propanol-water mixture, acetyl tributyl citrate (ATBC) was added and stirred for 1 hour. The resulting solution was used for coating of Naltrexone loaded IR-69F resinate.

Figure 11:
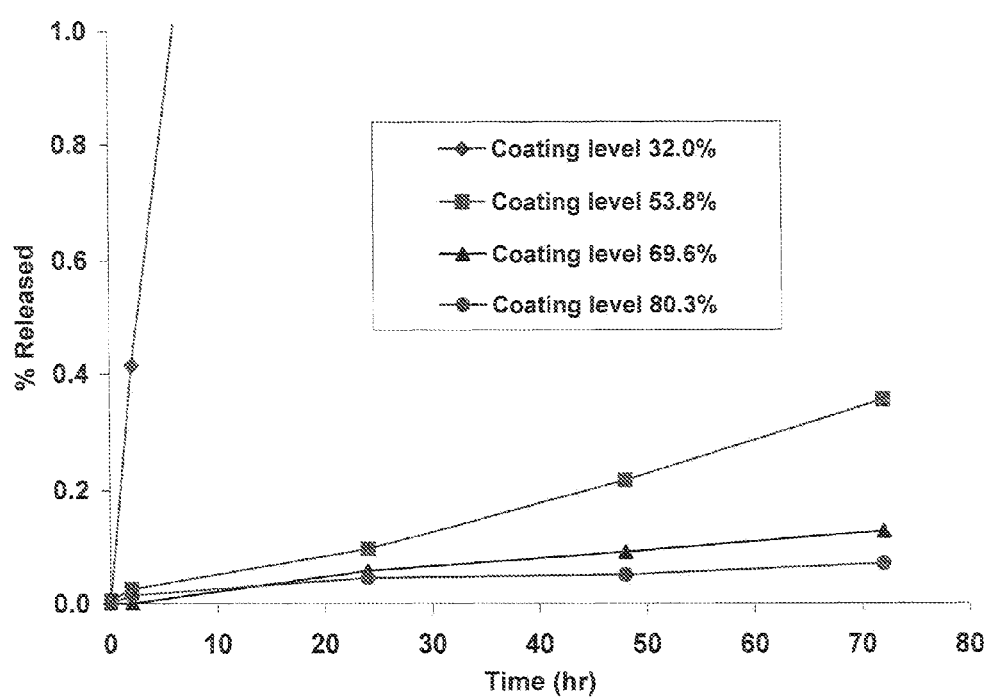
FIG. 11 is a line graph showing the release of Naltrexone from Naltrexone IR-69F resinate coated with different levels of ethylcellulose.

TPTA release from the coated naltrexone loaded IR-69F resinate in 75 ml of 0.1 N HO for the first 2 hours, then in phosphate buffer (pH 6.8) for the remaining 70 hours using USP Apparatus II at 50 rpm, was determined. Dissolution samples were analyzed using a validated HPLC assay. The dissolution profiles of naltrexone from naltrexone loaded IR-69F resinate with different coating levels are shown in FIG. 11. The dissolution profiles indicate that naltrexone release rate gradually decreased as the coating level increased. When the coating level reached 80%, less than 0.1% TPTA was released in 72 hours.

Example 7

Use of a pH Dependent Polymer as a Cushioning Agent TPTA Trap

Four different viscous gels were prepared from blends of Eudragit® E (Rohm Pharma GmbH, Darmstadt, Germany) and one of the following four solvent plasticizers: triethyl citrate (TEC), acetyl triethyl citrate (ATEC), tributyl citrate (TBC), and acetyl tributyl citrate (ATBC). Approximately, 2 grams of each gel were well mixed with approximately 2 grams of oxycodone loaded resinate (20% of TPTA loading). Approximately 0.8 gram of the resulting mixture (containing 80 mg of oxycodone) were loaded into hard gelatin capsules (00 size). Eudragit® E can be dissolved only at low pH, such as is present in the stomach. After dissolution of the polymer, the resinate was exposed to GI fluid to release the TPTA.

TPTA release from the capsules was determined in simulated gastric fluid using a USP apparatus II (paddle method) at 50 rpm.

Figure 12:
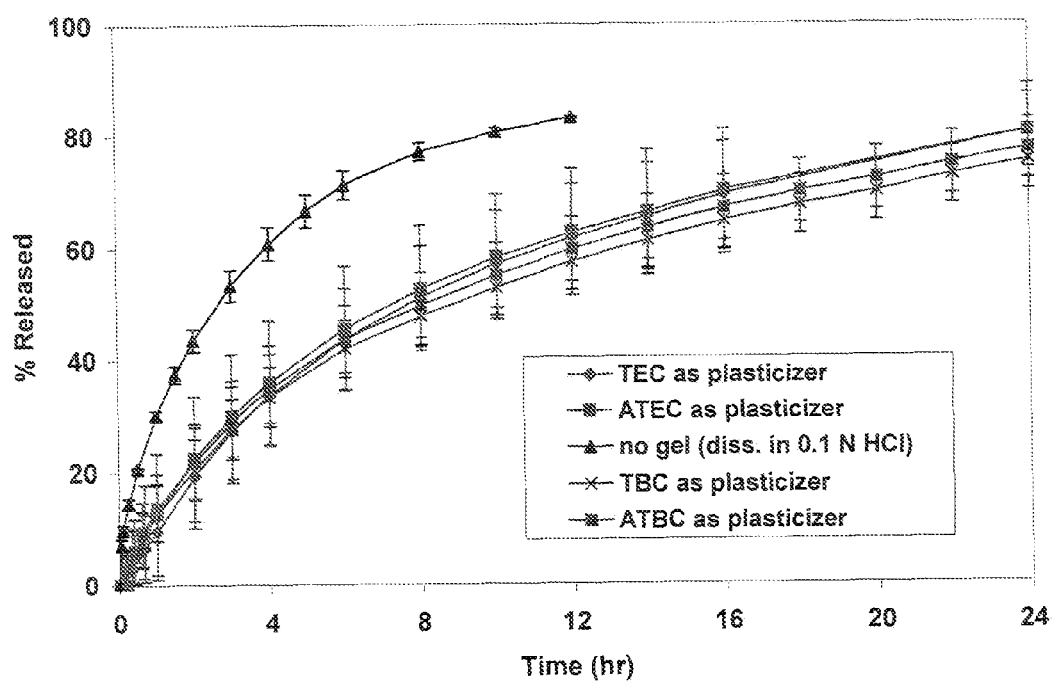
FIG. 12 is a line graph showing the in vitro release of oxycodone from oxycodone resinate suspended in gels prepared from blends of Eudragit® E and different plasticizers.

TPTA release from the resinate suspended in the gels prepared with Eudragit® E and from a control formulation lacking a gel is shown in FIG. 12. As shown in FIG. 12, TPTA release rate from the formulations containing the gel was slightly less rapid compared to that from the control formulation. This example shows that the presence of the Eudragit® E ion exchange resin trap does not markedly decrease release of a TPTA from a resinate when the TPTA is taken as intended by oral administration. The presence of the gel makes it difficult to crush or masticate the resinate and extract the TPTA from the resinate for illicit use.

Following is Table 2 that includes Examples 8 to 10 and compares several types of TPTA traps based on mechanism of action to reduce or retard burst release of a drug, such as a TPTA, from a dosage form. Table 2 compares the mechanism of action and the desired physical and/or chemical properties of the TPTA trap, and lists examples of dosage forms that may be used with the different types of TPTA traps.

TABLE 2

| TYPE OF TPTA TRAP | DESIRED OUTCOME UPON PHYSICAL TAMPERING | DESIRED PROPERTIES OF TRAP (Not all properties required) | DOSAGE FORM | EXAMPLES 8 to 10—These examples are for reduction or retardation of dose dumping from a TPTA composition in vivo or in vitro |
|---|---|---|---|---|
| Example 8— CUSHIONING AGENT | Reduce fracturing of TPTA composition | Softer/more elastic/more plastic than TPTA composition | Hard shell capsule | First population of beads are microencapsulated glycerol ester of wood rosin (rosin resin) particles plasticized with a plasticizer(s) as TPTA trap Second population of beads are TPTA loaded ion exchange resinate as TPTA composition. Efficient crushing of TPTA loaded ion exchange resinates is prevented because of the cushioning effect of the rosin particles. Ion exchange is also reduced due to insoluble rosin blocking access of solution ions to binding sites of resinate and TPTA diffusion out of resinate. |
| | | | Hard shell capsule | First population of beads are microparticles prepared from a masticatory elastomer with or without a plasticizer(s) as TPTA trap Second population of beads are drug loaded ion exchange resinates as TPTA composition. Efficient crushing of TPTA loaded ion exchange resinates is prevented since the resinate embeds (is stuck) into the elastomer upon chewing or crushing. This reduces access of an ionic medium to the resinate binding sites to extract the TPTA. |
| | | | Tablet-bilayer | One layer is elastomer composition as TPTA trap. Another layer is the mixture of TPTA loaded TPTA resinate with necessary excipients. When the tablet is crushed, the TPTA trap works to reduce dose dumping in an in vivo or in vitro medium by embedding the resinate into trap, thereby preventing efficient crushing and coating to resinate thereby reducing TPTA release. |
| | | | Liquid filled capsule | Capsules are filled with a mixture of TPTA loaded ion exchange resinates as TPTA composition and plasticized Eurdragit E, or Eurdragit L or Eurdragit S, cellulose acetate phthalate, polyvinylacetate phthalate as a TPTA trap. Release of the loaded TPTA does not change significantly |

TABLE 2-continued

| TYPE OF TPTA TRAP | DESIRED OUTCOME UPON PHYSICAL TAMPERING | DESIRED PROPERTIES OF TRAP (Not all properties required) | DOSAGE FORM | EXAMPLES 8 to 10—These examples are for reduction or retardation of dose dumping from a TPTA composition in vivo or in vitro |
|---|---|---|---|---|
| | | | | when the capsules are crushed since the Eudragit gel retards access to the ionic medium and prevents efficient crushing of the resinate. |
| | | | Hard shell capsule | First population of beads are a masticatory elastomer and rosin resin spheronized as TPTA trap coated with plasticized Eurdragit E, or Eurdragit L or Eurdragit S, cellulose acetate phthalate, polyvinylacetate phthalate. Second population of beads are TPTA resinate particles as a TPTA composition which is coated or layered onto the TPTA trap beads. Fracturing of resinate is reduced due to imbedding of resinate into trap upon physical tampering |
| | | | Hard shell capsule | First population of beads are a masticatory elastomer and rosin resin spheronized as TPTA trap. Second population of beads are a masticatory elastomer combined with antagonist to the TPTA and second TPTA trap. Particle is coated to be non-permeable/dissolvable in GI tract Third population is a TPTA resinate as TPTA composition. Chewing releases soluble antagonist (similar to flavor in chewing gum being released while insoluble resin is imbedded into elastomer and will not release. |
| | | | Hard shell capsule | First population of beads are elastomer and terpene resin spheronized as TPTA trap Second population of beads are a TPTA composition not susceptible to crushing which may be formulated via the methods presented in U.S. patent application 2005/0236741 TPTA release from TPTA composition is retarded due to embedding into trap upon physical tampering |
| | | | Hard shell capsule | First population of beads are a masticatory elastomer composition + aversive agent as one bead coated to be non-releasable in GI fluid. Ion exchange resinate (possibly sub 20 microns) overcoated onto the TPTA trap bead Chewing embeds ion exchange resin and releases water soluble aversive agent into saliva of mouth |
| Example 9— BLOCKING AGENT | Reduces or retards dose dumping from TPTA composition | Coating/ agglomerating/ hydrophobic/ limited water solubility/ tacky/surface | Hard shell capsule | First population of beads are microcapsules of Carbopol ® (powder or granulated with or without suitable additives) as a TPTA trap Second population of beads |

TABLE 2-continued

| TYPE OF TPTA TRAP | DESIRED OUTCOME UPON PHYSICAL TAMPERING | DESIRED PROPERTIES OF TRAP (Not all properties required) | DOSAGE FORM | EXAMPLES 8 to 10—These examples are for reduction or retardation of dose dumping from a TPTA composition in vivo or in vitro |
|---|---|---|---|---|
| | | area decreasing/ gelling hydrophobicity increasing/ limited water permeability | | are microcapsules of water which are an activator of Carbopol ® Third population of beads are TPTA loaded resinates as TPTA composition. Upon crushing of the capsules, the encapsulated water is released. This released water reacts with the released Carbopol ® and forms an adhesive gel matrix which surrounds the resinate and slows down the penetration of an ionic medium to release the TPTA. |
| | | | Hard shell capsule | First population of Eudragit coated wax beads with or without a softening agent -as TPTA trap TPTA loaded ion exchange resinate as TPTA composition. Crushing of the capsules embeds the resinate into the wax beads and slows down the release of TPTA from ion exchange resinates. |
| | | | Bilayer tablet | First layer masticatory elastomer as TPTA trap Second layer TPTA loaded ion exchange resinate as TPTA composition Crushing the tablet results in decreased or non-burst release of the TPTA since the resinates are embedded into the wax layer and slow down the release of the bound TPTA from the resinates |
| | | | Trilayer tablet | First layer is a masticatory elastomer as TPTA trap Second layer is TPTA loaded ion exchange resinate as TPTA composition Third layer is a masticatory elastomer as TPTA trap Chewing embeds resinate into insoluble TPTA trap and burst release is reduced. |
| | | | Dual core tablet | Inner core is rosin resin as TPTA trap. Outer core is ion exchange resinate as TPTA composition. Chewing embeds resinate into insoluble TPTA trap and burst release is reduced. |
| | | | Hard shell capsule | Sucrose Acetate Isobutyrate (SAIB) based TPTA composition as one population of beads. Unloaded (non TPTA containing) SAIB/CAB beads coated with non-water soluble coating as TPTA trap and second population of beads Crushing beads together increases the hydrophobicity of the combined mass and decreases surface area as compared to individual particles resulting in less |

TABLE 2-continued

| TYPE OF TPTA TRAP | DESIRED OUTCOME UPON PHYSICAL TAMPERING | DESIRED PROPERTIES OF TRAP (Not all properties required) | DOSAGE FORM | EXAMPLES 8 to 10—These examples are for reduction or retardation of dose dumping from a TPTA composition in vivo or in vitro |
|---|---|---|---|---|
| | | | Hard shell capsule | diffusion area for the TPTA to enter biological fluid. Result is decreased burst release. Sucrose Acetate Isobuytrate (SAIB) based TPTA composition as one population of beads. Loaded (TPTA containing) SAIB/CAB beads coated with water soluble or permeable coating as TPTA trap and second population of beads. Crushing beads together increases the hydrophobicity of the combined mass and decreases surface area as compared to individual particles resulting in less diffusion area for the TPTA to enter biological fluid. Result is decreased burst release of TPTA. |
| | | | Liquid | Terpene resins microencapsulated and coated as TPTA trap. Second population of sub 50 micron TPTA resinate. Resinate coated as per Raghunathan U.S. Pat. No. 4,221,778 as TPTA composition. Both populations are suspended in a liquid vehicle. Separation of TPTA composition from TPTA trap is difficult. If done and the populations are crushed together, the resinate is protected from fracturing and dose dumping of TPTA is retarded. |
| Example 10—COMPETITIVE AGENT | Complexes with ionically charged TPTA or ion exchange material | Ionically accommodating | Hard shell capsule | First population of beads are microencapsulated ionically charged gel such as calcium alginate as TPTA trap. Second population of beads are TPTA resinate as TPTA composition Crushing coats and embeds the resinate into the calcium alginate. In an ion solution, such as acid, the H+ ions are traversing through the charged alginate mass and displacing the Ca++ ion. Diffusion of the TPTA out of resinate is slowed since the TPTA is also being complexed by the alginate |

Further modifications, uses, and applications of the invention described herein will be apparent to those skilled in the art. It is intended that such modifications be encompassed in the following claims.

The invention claimed is:

1. A method for making a dosage form comprising combining a drug and a TPTA (Tamper Prone Therapeutic Agent) trap, thereby obtaining a dosage form comprising a drug and a TPTA (Tamper Prone Therapeutic Agent) trap, wherein the dosage form comprises a multiplicity of subunits and/or layers, and wherein the drug and the TPTA trap are maintained separately in different subunits or layers of the dosage form, and wherein if the TPTA trap comprises a gelling agent, the TPTA trap comprises a TPTA trap activator and the gelling agent and the TPTA trap activator are sequestered from each other.

2. The method of claim 1 wherein the drug is associated with a resin as a resinate.

3. The method of claim 2 wherein the resinate is made by mixing a drug in solution or suspension with an ion exchange resin at a temperature and for a time sufficient for the drug and the ion exchange resin to associate and form the resinate.

4. The method of claim 1 wherein the TPTA trap is a cushioning agent, a blocking agent, or a competitive agent.

5. The method of claim 4 wherein the TPTA trap is a cushioning agent comprising one or more materials selected from the group consisting of wax or wax-like material, elastomeric masticatory substance, rosin resin or rosin resin derivative, terpene resin or terpene resin derivative, pH dissolution dependent polymer, and ethyl cellulose or cellulose derivative.

6. The method of claim 4 wherein the TPTA trap is a blocking agent comprising one or more materials selected from the group consisting of polymer of acrylic acid crosslinked with allyl sucrose or allylpentaerythritol, acrylic polymers, neutral glucan, a hydrocolloid or mixture of hydrocolloids, citric acid ester, and sucrose resin.

7. The method of claim 4 wherein the TPTA trap is a competitive agent comprising one or more materials selected from the group of polyelectrolyte hydrogel, or a complex or coacervate of polyelectrolyte hydrogels, or an ion exchange material that is not complexed to the TPTA in The method and that is barrier coated with a water impermeable coating.

* * * * *